「12」 United States Patent
Murphy et al.

(10) Patent No.: US 9,358,236 B2
(45) Date of Patent: Jun. 7, 2016

(54) COMBINATIONS OF THERAPEUTIC AGENTS FOR USE IN THE TREATMENT OF NEURODEGENERATIVE DISEASES

(75) Inventors: Leon Murphy, Newton, MA (US); Jvan Galimberti, Bellinzona (CH)

(73) Assignee: Novartis AG, Basel (CH)

( * ) Notice: Subject to any disclaimer, the term of this patent is extended or adjusted under 35 U.S.C. 154(b) by 220 days.

(21) Appl. No.: 13/985,346

(22) PCT Filed: Feb. 14, 2012

(86) PCT No.: PCT/IB2012/050669
§ 371 (c)(1),
(2), (4) Date: Aug. 14, 2013

(87) PCT Pub. No.: WO2012/110953
PCT Pub. Date: Aug. 23, 2012

(65) Prior Publication Data
US 2013/0331388 A1    Dec. 12, 2013

Related U.S. Application Data

(60) Provisional application No. 61/443,493, filed on Feb. 16, 2011.

(51) Int. Cl.
*A61K 31/4745* (2006.01)
*A61K 31/445* (2006.01)
*A61K 31/5377* (2006.01)
*A61K 31/436* (2006.01)
*A61K 31/496* (2006.01)
*A61K 31/52* (2006.01)
*A61K 45/06* (2006.01)

(52) U.S. Cl.
CPC ........... *A61K 31/5377* (2013.01); *A61K 31/436* (2013.01); *A61K 31/4745* (2013.01); *A61K 31/496* (2013.01); *A61K 31/52* (2013.01); *A61K 45/06* (2013.01)

(58) Field of Classification Search
None
See application file for complete search history.

(56) References Cited

U.S. PATENT DOCUMENTS

2010/0233733 A1*  9/2010  Fantl ..................... 435/7.23

FOREIGN PATENT DOCUMENTS

| WO | 2006/122806 A2 | 11/2006 |
| WO | 2008/103636 A1 | 8/2008 |
| WO | WO 2008103636 A1 * | 8/2008 |
| WO | WO 2010049481 A1 * | 5/2010 |
| WO | 2010/049481 A1 | 6/2010 |
| WO | 2010/118419 A2 | 10/2010 |
| WO | 2010/129622 A1 | 11/2010 |

OTHER PUBLICATIONS

Dello Russo, Cinzia et al., "Involvement of mTOR kinase in cytokine-dependent microglial activation and cell proliferation", Biochemical Pharmacology, vol. 78, No. 9, pp. 1242-1251, 2009.
Sarkar, Sovan et al., "A rational mechanism for combination treatment of Huntington's disease using lithium and rapamycin", Human Molecular Genetics, vol. 17, No. 2, pp. 170-178, 2008.
Pollizzi, Kristen et al. "Equivalent benefit of mTORCI blockade and combined PI#K-mTOR blockade in a mouse model of tuberous sclerosis." Molecular Cancer. BioMed Central Ltd. Jun. 15, 2009. 9 pages.
Sarkar, S. et al. "Rapamycin and mTOR-independent autophagy inducers ameliorate toxicity of polyglutamine-expanded huntingtin and related proteinopathies." Cell and Death Differentiation. Macmillan Publishers Limited. Jul. 18, 2008. pp. 46-56. 11 pages.

* cited by examiner

*Primary Examiner* — Svetlana M Ivanova
(74) *Attorney, Agent, or Firm* — Shawn D. Britt

(57) ABSTRACT

The present invention relates to a combination of an allosteric mTOR inhibitor and a catalytic mTOR inhibitor for use in the prevention or treatment of neurodegenerative diseases, for example Huntington's Disease, and products and pharmaceutical compositions comprising such a combination for use in the prevention or treatment of such neurodegenerative diseases.

4 Claims, 4 Drawing Sheets

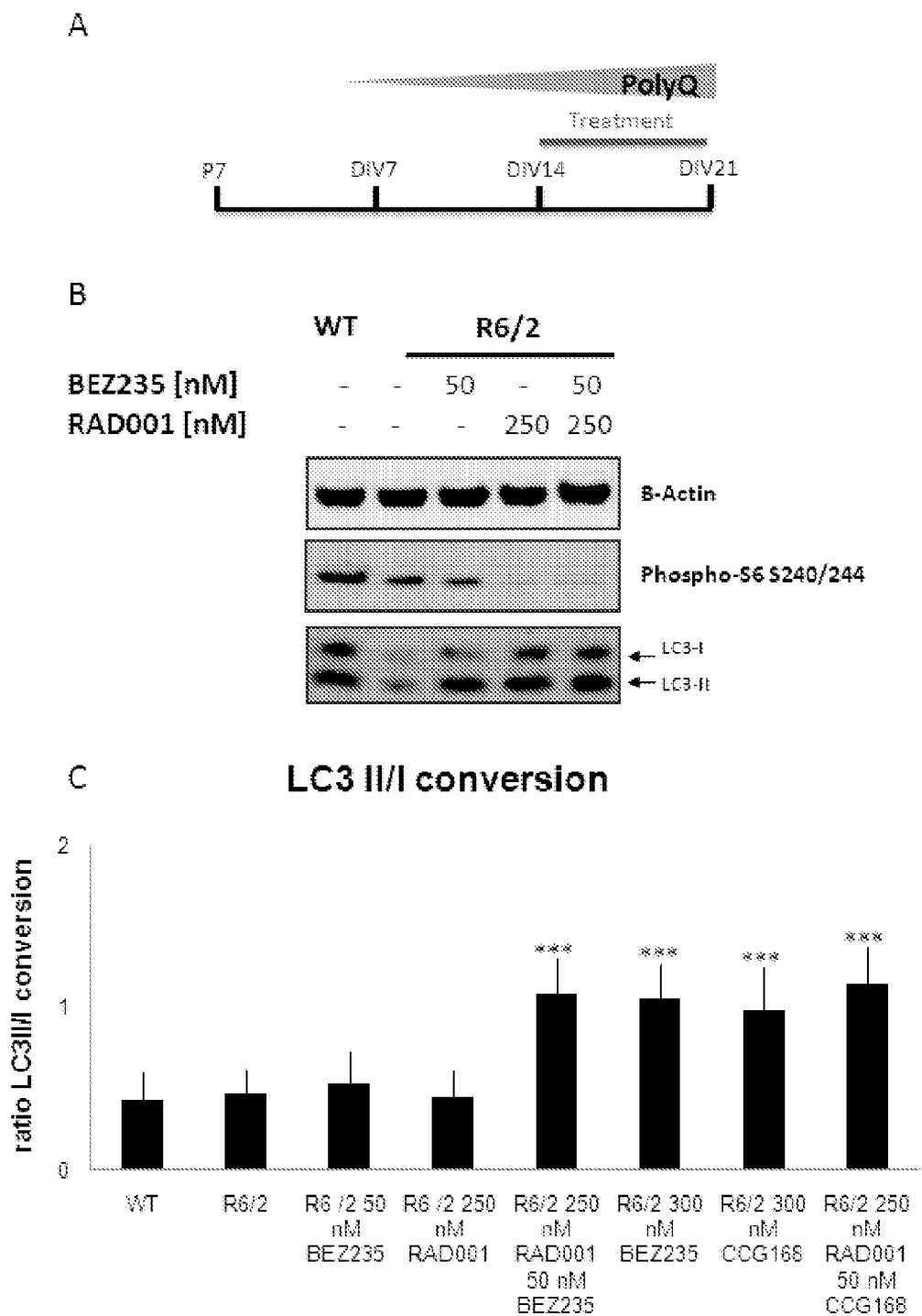
Figure 1: RAD001/BEZ235 or CCG168 combination induces autophagy in R6/2 brain slices.

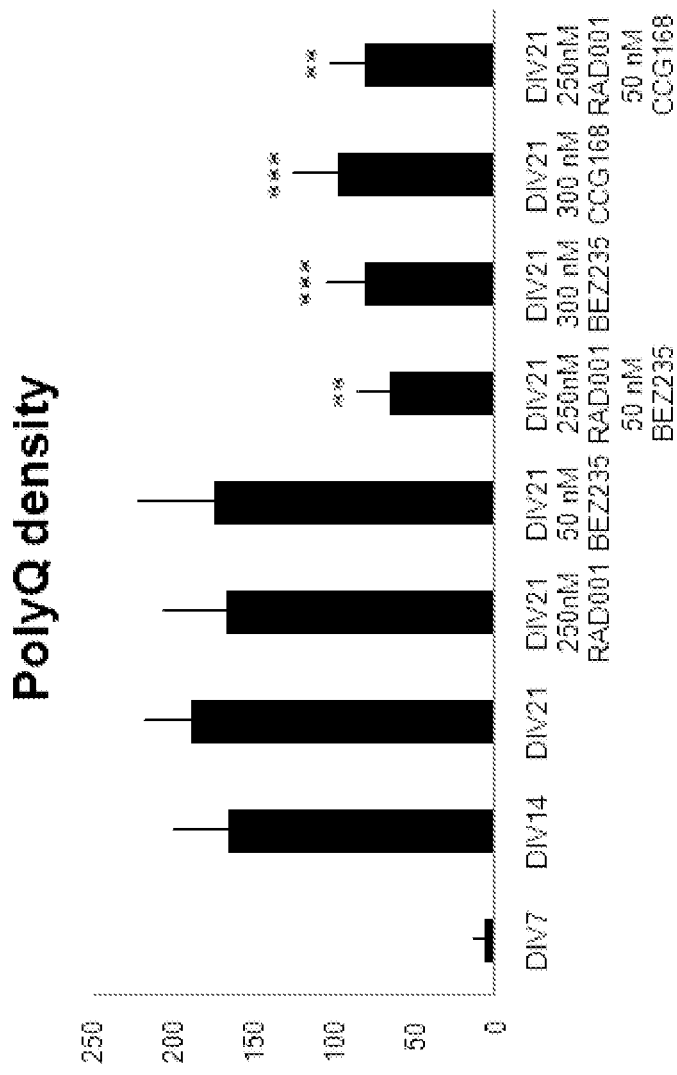
Figure 2: RAD001/BEZ235 or CCG168 combination reduces polyQ inclusions in R6/2 brain slices.

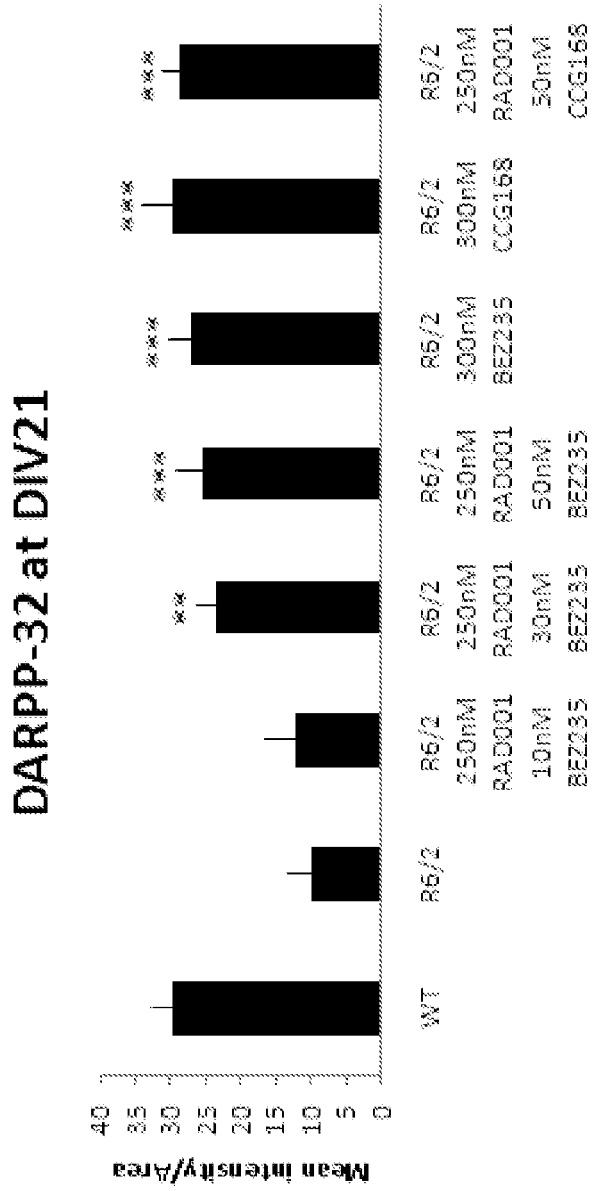
Figure 3: RAD001/BEZ235 or CCG168 combination prevents striatal degeneration in R6/2 brain slices as assessed by quantitative analysis of DARPP-32 intensity at DIV21.

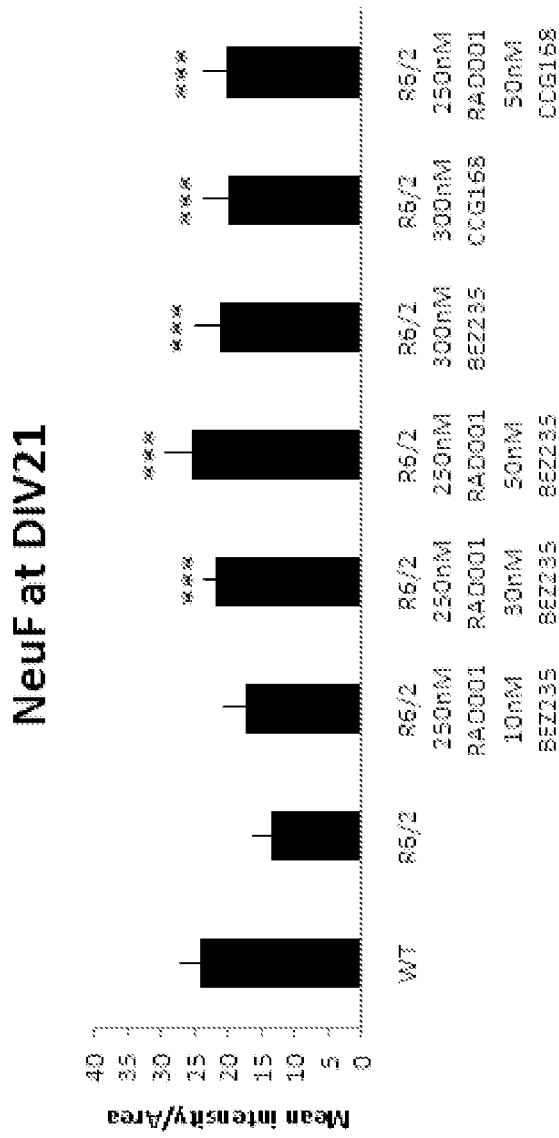
Figure 4: RAD001/BEZ235 or CCG168 combination prevents striatal degeneration in R6/2 brain slices as assessed by quantitative analysis of neurofilament intensity at DIV21.

COMBINATIONS OF THERAPEUTIC AGENTS FOR USE IN THE TREATMENT OF NEURODEGENERATIVE DISEASES

FIELD OF THE INVENTION

The present invention relates to a combination of therapeutic agents for use in the prevention or treatment of neurodegenerative diseases, for example Huntington's Disease, and products and pharmaceutical compositions comprising such a combination for use in the prevention or treatment of such neurodegenerative diseases.

In mammalian cells, the target of rapamycin (mTOR) kinase exists as a multiprotein complex described as the mTORC1 complex or mTORC2 complex, which senses the availability of nutrients and energy and integrates inputs from growth factors and stress signaling. The mTORC1 complex is sensitive to allosteric mTOR inhibitors such as rapamycin, is composed of mTOR, GβL, and regulatory associated proteins of mTOR (raptor), and binds to the peptidyl-prolyl isomerase FKBP12 protein (a FK506-binding protein 1A, 12 kDa). In contrast, the mTORC2 complex is composed of mTOR, GβL, and rapamycin-insensitive companion proteins of mTOR (rictor), and does not bind to the FKBP12 protein in vitro.

The mTORC1 complex has been shown to be involved in protein translational control, operating as a growth factor and nutrient sensitive apparatus for growth and proliferation regulation. mTORC1 regulates protein translation via two key downstream substrates: S6 kinase, which in turn phosphorylates ribosomal protein S6, and eukaryotic translation initiation factor 4E binding protein 1 (4EBP1), which plays a key role in modulating eIF4E regulated cap-dependent translation. The mTORC1 complex regulates cell growth in response to the energy and nutrient homeostasis of the cell, and the deregulation of mTORC1 is common in a wide variety of human cancers. The function of mTORC2 involves the regulation of cell survival via phosphorylation of Akt and the modulation of actin cytoskeleton dynamics.

The mTORC1 complex is sensitive to allosteric mTOR inhibitors such as rapamycin and derivatives in large part due to rapamycin's mode of action, which involves the formation of an intracellular complex with the FKBP12 and binding to the FKBP12-rapamycin binding (FRB) domain of mTOR. This results in a conformational change in mTORC1 which is believed to alter and weaken the interaction with its scaffolding protein raptor, in turn impeding substrates such as S6K1 from accessing mTOR and being phosphorylated. Rapamycin and rapalogues such as RAD001 have gained clinical relevance by inhibiting hyperactivation of mTOR associated with both benign and malignant proliferation disorders.

RAD001 is otherwise known as everolimus (Afinitor®), has the chemical name (1R,9S,12S,15R,16E,18R,19R,21R, 23S,24E,26E,28E,30S,32S,35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29, 35-hexamethyl-11,36-dioxa-4-aza-tricyclo[30.3.1.0$^{4,9}$] hexatriaconta-16,24,26,28-tetraene-2,3,10,14,20-pentaone and the following chemical structure

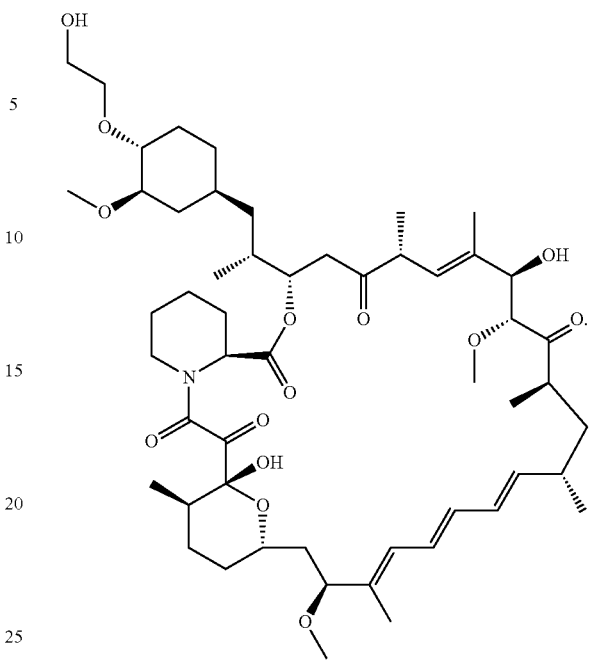

Everolimus is an FDA approved drug for the treatment of advanced kidney cancer and is still being investigated in several other phase III clinical trials in oncology. Preclinical studies have shown that Everolimus is able to inhibit the proliferation of a wide variety of tumor cell lines both in vitro and in vivo, presumably through the suppression of rapamycin sensitive mTORC1 function. Everolimus, as a derivative of rapamycin, is an allosteric mTOR inhibitor that is highly potent at inhibiting part of the mTORC1 function, namely S6 kinase (S6K) and the downstream S6K substrate S6. However, everolimus (and other rapamycin analogues) has little or no effect at inhibiting the priming phosphorylation events in 4EBP1 (T37/46), which is implicated as a key driver in tumorigenesis and maintenance. Allosteric mTOR inhibitors like everolimus (and other rapamycin analogues) have little or no effect at inhibiting the mTORC2 pathway, or its resulting activation of Akt signaling. Further examples of allosteric mTOR inhibitors include Sirolimus (rapamycin, AY-22989), 40-[3-hydroxy-2-(hydroxymethyl)-2-methyl propanoate]-rapamycin (also called Temsirolimus or CCI-779) and Deferolimus (AP-23573/MK-8669).

Alternatively, catalytic, ATP-competitive mTOR inhibitors have been found to target the mTOR kinase domain directly and target both mTORC1 and mTORC2. These are also more effective inhibitors of mTORC1 than such allosteric mTOR inhibitors as rapamycin, because they modulate rapamycin-resistant mTORC1 outputs such as 4EBP1-T37/46 phosphorylation and cap-dependent translation.

BEZ235 is a catalytic mTOR inhibitor, having the chemical name 2-methyl-2-[4-(3-methyl-2-oxo-8-quinolin-3-yl-2, 3-dihydro-imidazo[4,5-c]quinolin-1-yl)-phenyl]-propionitrile and the following chemical structure

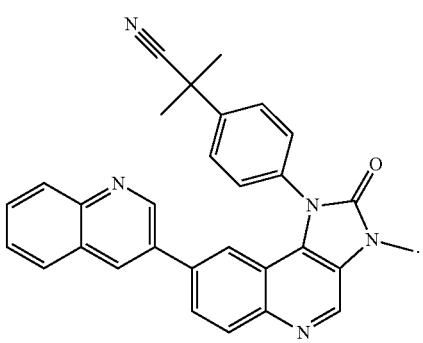 [SMILES: Cn1c(=O)n(-c2ccc(C(C)(C)C#N)cc2)c2c3cc(-c4cnc5ccccc5c4)ccc3ncc21]

BEZ235 may also be used in its monotosylate salt form. The synthesis of BEZ235 is described in WO2006/122806.

As a catalytic mTOR inhibitor BEZ235 is capable of shutting down the complete function of mTORC1 complex, including both the rapamycin sensitive (phosphorylation of S6K, and subsequently phosphorylation of S6) and rapamycin insensitive (phosphorylation of 4EBP1) functions. BEZ235 has a differential effect according to the drug concentration used, whereby mTOR inhibition predominates at a low concentration (less than 100 nmol/L) but dual PI3K/mTOR inhibition at relatively higher concentrations (approximately 500 nmol/L), Serra et al., 2008.

A further catalytic mTOR inhibitor described in the literature is CCG168 (otherwise known as AZD-8055, Chresta et al., 2010) which has the chemical name {5-[2,4-bis-((S)-3-methyl-morpholin-4-yl)-pyrido[2,3d]pyrimidin-7-yl]-2-methoxy-phenyl}-methanol and the following chemical structure

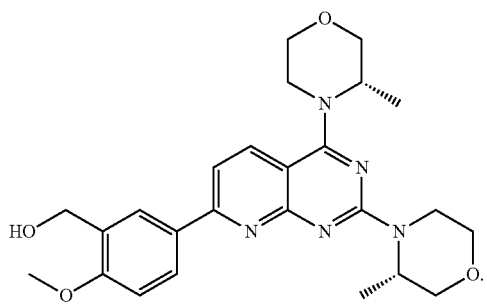 [SMILES: COc1ccc(-c2ccc3c(N4CCOC[C@@H]4C)nc(N4CCOC[C@@H]4C)nc3n2)cc1CO]

Further examples of catalytic mTOR inhibitors include 8-(6-methoxy-pyridin-3-yl)-3-methyl-1-(4-piperazin-1-yl-3-trifluoromethyl-phenyl)-1,3-dihydro-imidazo[4,5-c]quinolin-2-one (WO2006/122806), Ku-0063794 (Garcia-Martinez et al., 2009) and WYE-354 (Yu et al., 2009).

Huntington's disease (HD) is characterized by a selective neuronal cell death in cortex and striatum which leads to progressive dementia, motor impairment, and personality changes. A major molecular feature in HD is the gradual appearance of cytosolic and nuclear polyQ inclusions which runs in parallel to disease onset and progression. In the striatum, medium-sized spiny neurons (MNs) exhibit a gradual increase of polyQ inclusions, decrease of DARPP-32 and global axonal degeneration (The Huntington's Disease Collaborative Research Group. 1993; Davies et al., 1997; Bibb et al., 2000; Luthi-Carter et al., 2000). To follow striatal degeneration, an ex-vivo model for Huntington's disease has been developed using corticostriatal slice cultures from the R6/2 mouse model. This approach is based on the interface method and yields slice cultures that can be maintained for several weeks (Galimberti et al., 2006; Gogolla et al., 2006; Galimberti et al., 2010). When the R6/2 slices were investigated at different weeks in vitro, a gradual increase of polyQ inclusions, a decrease of DARPP-32 and a global neurofilament loss in the striatum was observed.

As described herein, studies in R6/2 slices were initiated to investigate whether the clearance of mutant Huntingtin (mHtt) is sufficient to preserve striatal degeneration. In particular, autophagy was induced by inhibiting the mTOR pathway from 14 to 21 days in vitro (DIV). mTOR inhibition induced autophagy, reduced polyQ inclusions and preserved DARPP-32 and neurofilament loss in striatum. Interestingly, a low-dose combination of an allosteric mTOR inhibitor (RAD001) and a catalytic mTOR inhibitor (BEZ235 or CCG168) worked synergistically compared to 250 nM RAD001 and 50 nM BEZ235 single treatment. Moreover, the combinatorial mTOR inhibition of 250 nM RAD001/30 nM BEZ235 preserved striatal degeneration at a 10-fold lower BEZ235 concentration. Thus, the results described herein suggest that low-dose combinations of an allosteric mTOR inhibitor and a catalytic mTOR inhibitor reduce striatal degeneration in R6/2 slices and represent a therapeutic opportunity for HD treatment. This unexpected synergistic interaction allows a reduction in the required dose, leading to fewer side effects and enhancement of clinical effectiveness.

In addition to HD, other neurodegenerative diseases caused by aggregate-prone proteins could also be treated by autophagy induction via inhibition of the mTOR pathway, for example Parkinson's disease, spinocerebellar ataxia type 3 (also known as Machado-Joseph disease), Alzheimer's disease, motor neuron disease caused by mutations in superoxide dismutase 1 and forms of peripheral neuropathy caused by mutations in peripheral myelin protein 22. For further description of the link between autophagy and neurodegeneration see Rubinsztein D C et al., 2007 and Sarkar S et al., 2009.

SUMMARY OF THE INVENTION

In a first aspect of the invention, there is therefore provided a combination of an allosteric mTOR inhibitor and a catalytic mTOR inhibitor for use in the treatment or prevention of a neurodegenerative disease.

In another aspect, the invention relates to the use of an allosteric mTOR inhibitor and a catalytic mTOR inhibitor for the manufacture of a medicament for the treatment or prevention of a neurodegenerative disease.

In a further aspect, the invention relates to the use of a combination of an allosteric mTOR inhibitor and a catalytic mTOR inhibitor as active pharmaceutical ingredients in a medicament for the treatment or prevention of a neurodegenerative disease.

In a further aspect of the invention, there is provided a method for the treatment or prevention of a neurodegenerative disease in a subject in need of such treatment or prevention, which method comprises administering to such subject an effective amount of a combination of an allosteric mTOR inhibitor and a catalytic mTOR inhibitor.

In another aspect of the invention, there is provided a combination product comprising an allosteric mTOR inhibitor and a catalytic mTOR inhibitor for simultaneous, separate or sequential use in the treatment or prevention of a neurodegenerative disease.

In another aspect of the invention, there is provided a pharmaceutical composition comprising:

an allosteric mTOR inhibitor;
a catalytic mTOR inhibitor; and
a pharmaceutically acceptable carrier or diluent;
for use in the treatment or prevention of a neurodegenerative disease.

DETAILED DESCRIPTION OF THE FIGURES

FIG. 1: RAD001/BEZ235 or CCG168 combination induces autophagy in R6/2 brain slices.

(A) Schematic description of treatment in brain slices. Slices were prepared at postnatal day 7 (P7) and treated with RAD001, BEZ235 and CCG168 from DIV14 to DIV21.

(B) Biochemical analysis of mTORC1 activity (p-S6 S240/244), autophagy induction (LC3-II/I conversion) and B-actin. Treatment with 50 nM BEZ235 did not reduce p-S6 S240/244 and had no effect in increasing the LC3-II/I conversion (LC3-II/I ratio). However, 250 nM RAD001 and 250 nM RAD001/50 nM BEZ235 reduced p-S6 S240/244 and the combination of both additionally increased the LC3-II level.

(C) Quantitative analysis of the LC3-II/I conversion (LC3-II/I ratio). Note that the combination of RAD001/BEZ235 induced a significant LC3-II/I conversion compared to single low concentrations. 300 nM BEZ235 and 300 nM CCG168 reached similar efficacy, indicating that BEZ235 or CCG168 together with RAD001 synergistically induce autophagy (N=5 slices for each condition, one-way ANOVA p<0.01, Post hoc Student's t test, *p<0.001)

FIG. 2: RAD001/BEZ235 or CCG168 combination reduces polyQ inclusions in R6/2 brain slices.

Quantification of the polyQ density from DIV7 to DIV21 and under different treatments at DIV21. The combination of RAD001/BEZ235 reduced 40%±11 of the polyQ density compared to the DIV21 R6/2 DMSO treated slices, whereas 250 nM RAD001 and 50 nM BEZ235 single concentrations showed no effect. The combination of RAD001/CCG168 also reduced the polyQ density compared to the DIV21 R6/2 DMSO treated slices. (N=5 slices for each condition, one-way ANOVA *p<0.05, Post hoc Student's t test, ***p<0.001)

FIG. 3: RAD001/BEZ235 or CCG168 combination prevents striatal degeneration in R6/2 brain slices as assessed by quantitative analysis of DARPP-32 intensity at DIV21.

The combination of RAD001/BEZ235 preserved 80%±5 of the DARPP-32 level compared to control R6/2 slices. The combination of RAD001/CCG168 was also effective at preserving DARPP-32 levels. (N=5 slices for each condition, one-way ANOVA p<0.01, Post hoc Student's t test, p<0.01; ***p<0.001)

FIG. 4: RAD001/BEZ235 or CCG168 combination prevents striatal degeneration in R6/2 brain slices as assessed by quantitative analysis of neurofilament intensity at DIV21.

The combination of RAD001/BEZ235 preserved 95%±12 of the neurofilament level compared to control R6/2 slices. The combination of RAD001/CCG168 was also effective at preserving neurofilament levels. (N=5 slices for each condition, one-way ANOVA p<0.01, Post hoc Student's t test, p<0.01; ***p<0.001)

DETAILED DESCRIPTION OF THE INVENTION

In a first aspect of the invention, there is therefore provided a combination of an allosteric mTOR inhibitor and a catalytic mTOR inhibitor for use in the treatment or prevention of a neurodegenerative disease.

In one embodiment, there is provided a combination of an allosteric mTOR inhibitor and a catalytic mTOR inhibitor for use in the treatment or prevention of a neurodegenerative disease wherein the allosteric mTOR inhibitor is selected from RAD001, Sirolimus, Temsirolimus and Deferolimus, and the catalytic mTOR inhibitor is selected from BEZ235, CCG168, Ku-0063794, WYE-354 and 8-(6-methoxy-pyridin-3-yl)-3-methyl-1-(4-piperazin-1-yl-3-trifluoromethylphenyl)-1,3-dihydro-imidazo[4,5-c]quinolin-2-one.

In one embodiment, there is provided a combination of RAD001 and BEZ235 or CCG168 for use in the treatment or prevention of a neurodegenerative disease.

In one embodiment, there is provided a combination of RAD001 and BEZ235 or CCG168 for use in the treatment or prevention of a neurodegenerative disease wherein the RAD001 or CCG168 is administered at a dose of about 1.5 mg/kg/day and the BEZ235 is administered at a dose of about 2.5 mg/kg/day.

In one embodiment, there is provided a combination of RAD001 and BEZ235 or CCG168 for use in the treatment or prevention of neurodegenerative disease wherein:
the RAD001 is administered at a dose of between 1.4 and 1.6 mg/kg/day and the BEZ235 or CCG168 is administered at a dose of between 2.4 and 2.6 mg/kg/day;
the RAD001 is administered at a dose of between 1.3 and 1.7 mg/kg/day and the BEZ235 or CCG168 is administered at a dose of between 2.3 and 2.7 mg/kg/day;
the RAD001 is administered at a dose of between 1.2 and 1.8 mg/kg/day and the BEZ235 or CCG168 is administered at a dose of between 2.2 and 2.8 mg/kg/day;
the RAD001 is administered at a dose of between 1.1 and 1.9 mg/kg/day and the BEZ235 or CCG168 is administered at a dose of between 2.1 and 2.9 mg/kg/day;
the RAD001 is administered at a dose of between 1.0 and 2.0 mg/kg/day and the BEZ235 or CCG168 is administered at a dose of between 2.0 and 3.0 mg/kg/day;
the RAD001 is administered at a dose of between 0.8 and 2.2 mg/kg/day and the BEZ235 or CCG168 is administered at a dose of between 1.8 and 2.6 mg/kg/day;
the RAD001 is administered at a dose of between 0.6 and 2.4 mg/kg/day and the BEZ235 or CCG168 is administered at a dose of between 1.6 and 2.8 mg/kg/day;
the RAD001 is administered at a dose of between 0.4 and 2.6 mg/kg/day and the BEZ235 or CCG168 is administered at a dose of between 1.4 and 3.0 mg/kg/day;
the RAD001 is administered at a dose of between 0.2 and 2.8 mg/kg/day and the BEZ235 or CCG168 is administered at a dose of between 1.0 and 3.5 mg/kg/day;
the RAD001 is administered at a dose of between 0.01 and 3.0 mg/kg/day and the BEZ235 or CCG168 is administered at a dose of between 0.5 and 4.0 mg/kg/day;
the RAD001 is administered at a dose of between 0.01 and 5.0 mg/kg/day and the BEZ235 or CCG168 is administered at a dose of between 0.01 and 5.0 mg/kg/day; or
the RAD001 is administered at a dose of between 0.01 and 10.0 mg/kg/day and the BEZ235 or CCG168 is administered at a dose of between 0.01 and 10.0 mg/kg/day.

In one embodiment, there is provided a combination of RAD001 and BEZ235 or CCG168 for use in the treatment or prevention of neurodegenerative disease wherein the RAD001 is administered at a dose of between 0.01 and 10.0 mg/kg/day and the BEZ235 or CCG168 is administered at a dose of between 0.01 and 10.0 mg/kg/day.

In another aspect, the invention relates to the use of an allosteric mTOR inhibitor and a catalytic mTOR inhibitor for the manufacture of a medicament for the treatment or prevention of a neurodegenerative disease.

In one embodiment, the invention relates to the use an allosteric mTOR inhibitor and a catalytic mTOR inhibitor for the manufacture of a medicament for the treatment or prevention of a neurodegenerative disease wherein the allosteric mTOR inhibitor is selected from RAD001, Sirolimus, Temsirolimus and Deferolimus, and the catalytic mTOR inhibitor is selected from BEZ235, CCG168, Ku-0063794, WYE-354 and 8-(6-methoxy-pyridin-3-yl)-3-methyl-1-(4-piperazin-1-yl-3-trifluoromethyl-phenyl)-1,3-dihydro-imidazo[4,5-c]quinolin-2-one.

In one embodiment, the invention relates to the use of RAD001 and BEZ235 or CCG168 for the manufacture of a medicament for the treatment or prevention of a neurodegenerative disease.

In one embodiment, the invention relates to the use of RAD001 and BEZ235 or CCG168 for the manufacture of a medicament for the treatment or prevention of a neurodegenerative disease wherein the RAD001 is administered at a dose of about 1.5 mg/kg/day and the BEZ235 or CCG168 is administered at a dose of about 2.5 mg/kg/day.

In one embodiment, the invention relates to the use of RAD001 and BEZ235 or CCG168 for the manufacture of a medicament for the treatment or prevention of a neurodegenerative disease wherein:
the RAD001 is administered at a dose of between 1.4 and 1.6 mg/kg/day and the BEZ235 or CCG168 is administered at a dose of between 2.4 and 2.6 mg/kg/day;
the RAD001 is administered at a dose of between 1.3 and 1.7 mg/kg/day and the BEZ235 or CCG168 is administered at a dose of between 2.3 and 2.7 mg/kg/day;
the RAD001 is administered at a dose of between 1.2 and 1.8 mg/kg/day and the BEZ235 or CCG168 is administered at a dose of between 2.2 and 2.8 mg/kg/day;
the RAD001 is administered at a dose of between 1.1 and 1.9 mg/kg/day and the BEZ235 or CCG168 is administered at a dose of between 2.1 and 2.9 mg/kg/day;
the RAD001 is administered at a dose of between 1.0 and 2.0 mg/kg/day and the BEZ235 or CCG168 is administered at a dose of between 2.0 and 3.0 mg/kg/day;
the RAD001 is administered at a dose of between 0.8 and 2.2 mg/kg/day and the BEZ235 or CCG168 is administered at a dose of between 1.8 and 2.6 mg/kg/day;
the RAD001 is administered at a dose of between 0.6 and 2.4 mg/kg/day and the BEZ235 or CCG168 is administered at a dose of between 1.6 and 2.8 mg/kg/day;
the RAD001 is administered at a dose of between 0.4 and 2.6 mg/kg/day and the BEZ235 or CCG168 is administered at a dose of between 1.4 and 3.0 mg/kg/day;
the RAD001 is administered at a dose of between 0.2 and 2.8 mg/kg/day and the BEZ235 or CCG168 is administered at a dose of between 1.0 and 3.5 mg/kg/day;
the RAD001 is administered at a dose of between 0.01 and 3.0 mg/kg/day and the BEZ235 or CCG168 is administered at a dose of between 0.5 and 4.0 mg/kg/day;
the RAD001 is administered at a dose of between 0.01 and 5.0 mg/kg/day and the BEZ235 or CCG168 is administered at a dose of between 0.01 and 5.0 mg/kg/day; or
the RAD001 is administered at a dose of between 0.01 and 10.0 mg/kg/day and the BEZ235 or CCG168 is administered at a dose of between 0.01 and 10.0 mg/kg/day.

In one embodiment, the invention relates to the use of RAD001 and BEZ235 or CCG168 for the manufacture of a medicament for the treatment or prevention of a neurodegenerative disease wherein the RAD001 is administered at a dose of between 0.01 and 10.0 mg/kg/day and the BEZ235 or CCG168 is administered at a dose of between 0.01 and 10.0 mg/kg/day.

In a further aspect, the invention relates to the use of a combination of an allosteric mTOR inhibitor and a catalytic mTOR inhibitor as active pharmaceutical ingredients in a medicament for the treatment or prevention of a neurodegenerative disease.

In one embodiment, the invention relates to the use of a combination of an allosteric mTOR inhibitor and a catalytic mTOR inhibitor as active pharmaceutical ingredients in a medicament for the treatment or prevention of a neurodegenerative disease wherein the allosteric mTOR inhibitor is selected from RAD001, Sirolimus, Temsirolimus and Deferolimus, and the catalytic mTOR inhibitor is selected from BEZ235, CCG168, Ku-0063794, WYE-354 and 8-(6-methoxy-pyridin-3-yl)-3-methyl-1-(4-piperazin-1-yl-3-trifluoromethyl-phenyl)-1,3-dihydro-imidazo[4,5-c]quinolin-2-one.

In one embodiment, the invention relates to the use of a combination of RAD001 and BEZ235 or CCG168 as active pharmaceutical ingredients in a medicament for the treatment or prevention of a neurodegenerative disease.

In one embodiment, the invention relates to the use of a combination of RAD001 and BEZ235 or CCG168 as active pharmaceutical ingredients in a medicament for the treatment or prevention of a neurodegenerative disease wherein the RAD001 is administered at a dose of about 1.5 mg/kg/day and the BEZ235 or CCG168 is administered at a dose of about 2.5 mg/kg/day.

In one embodiment, the invention relates to the use of a combination of RAD001 and BEZ235 or CCG168 as active pharmaceutical ingredients in a medicament for the treatment or prevention of a neurodegenerative disease wherein:
the RAD001 is administered at a dose of between 1.4 and 1.6 mg/kg/day and the BEZ235 or CCG168 is administered at a dose of between 2.4 and 2.6 mg/kg/day;
the RAD001 is administered at a dose of between 1.3 and 1.7 mg/kg/day and the BEZ235 or CCG168 is administered at a dose of between 2.3 and 2.7 mg/kg/day;
the RAD001 is administered at a dose of between 1.2 and 1.8 mg/kg/day and the BEZ235 or CCG168 is administered at a dose of between 2.2 and 2.8 mg/kg/day;
the RAD001 is administered at a dose of between 1.1 and 1.9 mg/kg/day and the BEZ235 or CCG168 is administered at a dose of between 2.1 and 2.9 mg/kg/day;
the RAD001 is administered at a dose of between 1.0 and 2.0 mg/kg/day and the BEZ235 or CCG168 is administered at a dose of between 2.0 and 3.0 mg/kg/day;
the RAD001 is administered at a dose of between 0.8 and 2.2 mg/kg/day and the BEZ235 or CCG168 is administered at a dose of between 1.8 and 2.6 mg/kg/day;
the RAD001 is administered at a dose of between 0.6 and 2.4 mg/kg/day and the BEZ235 or CCG168 is administered at a dose of between 1.6 and 2.8 mg/kg/day;
the RAD001 is administered at a dose of between 0.4 and 2.6 mg/kg/day and the BEZ235 or CCG168 is administered at a dose of between 1.4 and 3.0 mg/kg/day;
the RAD001 is administered at a dose of between 0.2 and 2.8 mg/kg/day and the BEZ235 or CCG168 is administered at a dose of between 1.0 and 3.5 mg/kg/day;
the RAD001 is administered at a dose of between 0.01 and 3.0 mg/kg/day and the BEZ235 or CCG168 is administered at a dose of between 0.5 and 4.0 mg/kg/day;
the RAD001 is administered at a dose of between 0.01 and 5.0 mg/kg/day and the BEZ235 or CCG168 is administered at a dose of between 0.01 and 5.0 mg/kg/day; or
the RAD001 is administered at a dose of between 0.01 and 10.0 mg/kg/day and the BEZ235 or CCG168 is administered at a dose of between 0.01 and 10.0 mg/kg/day.

In one embodiment, the invention relates to the use of a combination of RAD001 and BEZ235 or CCG168 as active pharmaceutical ingredients in a medicament for the treatment or prevention of a neurodegenerative disease wherein the RAD001 is administered at a dose of between 0.01 and 10.0 mg/kg/day and the BEZ235 or CCG168 is administered at a dose of between 0.01 and 10.0 mg/kg/day.

In a further aspect of the invention, there is provided a method for the treatment or prevention of a neurodegenerative disease in a subject in need of such treatment or prevention, which method comprises administering to such subject an effective amount of a combination of an allosteric mTOR inhibitor and a catalytic mTOR inhibitor.

In one embodiment, there is provided a method for the treatment or prevention of a neurodegenerative disease in a subject in need of such treatment or prevention, which method comprises administering to such subject an effective amount of a combination of an allosteric mTOR inhibitor and a catalytic mTOR inhibitor wherein the allosteric mTOR inhibitor is selected from RAD001, Sirolimus, Temsirolimus and Deferolimus, and the catalytic mTOR inhibitor is selected from BEZ235, CCG168, Ku-0063794, WYE-354 and 8-(6-methoxy-pyridin-3-yl)-3-methyl-1-(4-piperazin-1-yl-3-trifluoromethyl-phenyl)-1,3-dihydro-imidazo[4,5-c]quinolin-2-one.

In one embodiment, there is provided a method for the treatment or prevention of a neurodegenerative disease in a subject in need of such treatment or prevention, which method comprises administering to such subject an effective amount of a combination of RAD001 and BEZ235 or CCG168.

In one embodiment, there is provided a method for the treatment or prevention of a neurodegenerative disease in a subject in need of such treatment or prevention, which method comprises administering to such subject an effective amount of a combination of RAD001 and BEZ235 or CCG168 wherein the RAD001 is administered at a dose of about 1.5 mg/kg/day and the BEZ235 or CCG168 is administered at a dose of about 2.5 mg/kg/day.

In one embodiment, there is provided a method for the treatment or prevention of Huntington's a neurodegenerative disease in a subject in need of such treatment or prevention, which method comprises administering to such subject an effective amount of a combination of RAD001 and BEZ235 or CCG168 wherein:
the RAD001 is administered at a dose of between 1.4 and 1.6 mg/kg/day and the BEZ235 or CCG168 is administered at a dose of between 2.4 and 2.6 mg/kg/day;
the RAD001 is administered at a dose of between 1.3 and 1.7 mg/kg/day and the BEZ235 or CCG168 is administered at a dose of between 2.3 and 2.7 mg/kg/day;
the RAD001 is administered at a dose of between 1.2 and 1.8 mg/kg/day and the BEZ235 or CCG168 is administered at a dose of between 2.2 and 2.8 mg/kg/day;
the RAD001 is administered at a dose of between 1.1 and 1.9 mg/kg/day and the BEZ235 or CCG168 is administered at a dose of between 2.1 and 2.9 mg/kg/day;
the RAD001 is administered at a dose of between 1.0 and 2.0 mg/kg/day and the BEZ235 or CCG168 is administered at a dose of between 2.0 and 3.0 mg/kg/day;
the RAD001 is administered at a dose of between 0.8 and 2.2 mg/kg/day and the BEZ235 or CCG168 is administered at a dose of between 1.8 and 2.6 mg/kg/day;
the RAD001 is administered at a dose of between 0.6 and 2.4 mg/kg/day and the BEZ235 or CCG168 is administered at a dose of between 1.6 and 2.8 mg/kg/day;
the RAD001 is administered at a dose of between 0.4 and 2.6 mg/kg/day and the BEZ235 or CCG168 is administered at a dose of between 1.4 and 3.0 mg/kg/day;
the RAD001 is administered at a dose of between 0.2 and 2.8 mg/kg/day and the BEZ235 or CCG168 is administered at a dose of between 1.0 and 3.5 mg/kg/day;
the RAD001 is administered at a dose of between 0.01 and 3.0 mg/kg/day and the BEZ235 or CCG168 is administered at a dose of between 0.5 and 4.0 mg/kg/day;
the RAD001 is administered at a dose of between 0.01 and 5.0 mg/kg/day and the BEZ235 or CCG168 is administered at a dose of between 0.01 and 5.0 mg/kg/day; or
the RAD001 is administered at a dose of between 0.01 and 10.0 mg/kg/day and the BEZ235 or CCG168 is administered at a dose of between 0.01 and 10.0 mg/kg/day.

In one embodiment, there is provided a method for the treatment or prevention of Huntington's a neurodegenerative disease in a subject in need of such treatment or prevention, which method comprises administering to such subject an effective amount of a combination of RAD001 and BEZ235 or CCG168 wherein the RAD001 is administered at a dose of between 0.01 and 10.0 mg/kg/day and the BEZ235 or CCG168 is administered at a dose of between 0.01 and 10.0 mg/kg/day.

In another aspect of the invention, there is provided a combination product comprising an allosteric mTOR inhibitor and a catalytic mTOR inhibitor for simultaneous, separate or sequential use in the treatment or prevention of a neurodegenerative disease.

In one embodiment, there is provided a combination product comprising an allosteric mTOR inhibitor and a catalytic mTOR inhibitor for simultaneous, separate or sequential use in the treatment or prevention of a neurodegenerative disease wherein the allosteric mTOR inhibitor is selected from RAD001, Sirolimus, Temsirolimus and Deferolimus, and the catalytic mTOR inhibitor is selected from BEZ235, CCG168, Ku-0063794, WYE-354 and 8-(6-methoxy-pyridin-3-yl)-3-methyl-1-(4-piperazin-1-yl-3-trifluoromethyl-phenyl)-1,3-dihydro-imidazo[4,5-c]quinolin-2-one.

In one embodiment, there is provided a combination product comprising RAD001 and BEZ235 or CCG168 for simultaneous, separate or sequential use in the treatment or prevention of a neurodegenerative disease.

In one embodiment, there is provided a combination product comprising one or multiple doses of about 100 mg RAD001 and about 175 mg BEZ235 or CCG168 as either individual preparations or as a combined preparation for simultaneous, separate or sequential use in the treatment or prevention of a neurodegenerative disease.

In one embodiment, there is provided a combination product comprising one or multiple doses of 90 to 110 mg RAD001 and 165 to 185 mg BEZ235 or CCG168; 80 to 120 mg RAD001 and 155 to 195 mg BEZ235 or CCG168; 70 to 130 mg RAD001 and 145 to 205 mg BEZ235 or CCG168; 60 to 140 mg RAD001 and 135 to 215 mg BEZ235 or CCG168; 50 to 150 mg RAD001 and 125 to 225 mg BEZ235 or CCG168; 50 to 200 mg RAD001 and 100 to 300 mg BEZ235 or CCG168; 25 to 175 mg RAD001 and 100 to 250 mg BEZ235 or CCG168; 1 to 200 mg RAD001 and 50 to 300 mg BEZ235 or CCG168; 1 to 300 mg RAD001 and 1 to 500 mg BEZ235 or CCG168; or 1 to 500 mg RAD001 and 1 to 800 mg BEZ235 or CCG168; as either individual preparations or as a combined preparation for simultaneous, separate or sequential use in the treatment or prevention of a neurodegenerative disease.

In another aspect of the invention, there is provided a pharmaceutical composition comprising:
an allosteric mTOR inhibitor;
a catalytic mTOR inhibitor; and
a pharmaceutically acceptable carrier or diluent;

for use in the treatment or prevention of a neurodegenerative disease.

In one embodiment, there is provided a pharmaceutical composition comprising:
an allosteric mTOR inhibitor selected from RAD001, Sirolimus, Temsirolimus and Deferolimus;
a catalytic mTOR inhibitor selected from BEZ235, CCG168, Ku-0063794, WYE-354 and 8-(6-methoxy-pyridin-3-yl)-3-methyl-1-(4-piperazin-1-yl-3-trifluoromethyl-phenyl)-1,3-dihydro-imidazo[4,5-c]quinolin-2-one; and
a pharmaceutically acceptable carrier or diluent;
for use in the treatment or prevention of a neurodegenerative disease.

In one embodiment, there is provided a pharmaceutical composition comprising:
RAD001;
BEZ235 or CCG168; and
a pharmaceutically acceptable carrier or diluent;
for use in the treatment or prevention of a neurodegenerative disease.

In one embodiment, there is provided a pharmaceutical composition comprising:
about 100 mg RAD001;
about 175 mg BEZ235 or CCG168; and
a pharmaceutically acceptable carrier or diluent;
for use in the treatment or prevention of a neurodegenerative disease.

In one embodiment, there is provided a pharmaceutical composition comprising:
90 to 110 mg RAD001;
165 to 185 mg BEZ235 or CCG168; and
a pharmaceutically acceptable carrier or diluent;
for use in the treatment or prevention of a neurodegenerative disease.

In one embodiment, there is provided a pharmaceutical composition comprising:
80 to 120 mg RAD001;
155 to 195 mg BEZ235 or CCG168; and
a pharmaceutically acceptable carrier or diluent;
for use in the treatment or prevention of a neurodegenerative disease.

In one embodiment, there is provided a pharmaceutical composition comprising:
70 to 130 mg RAD001;
145 to 205 mg BEZ235 or CCG168; and
a pharmaceutically acceptable carrier or diluent;
for use in the treatment or prevention of a neurodegenerative disease.

In one embodiment, there is provided a pharmaceutical composition comprising:
60 to 140 mg RAD001;
135 to 215 mg BEZ235 or CCG168; and
a pharmaceutically acceptable carrier or diluent;
for use in the treatment or prevention of a neurodegenerative disease.

In one embodiment, there is provided a pharmaceutical composition comprising:
50 to 150 mg RAD001;
125 to 225 mg BEZ235 or CCG168; and
a pharmaceutically acceptable carrier or diluent;
for use in the treatment or prevention of a neurodegenerative disease.

In one embodiment, there is provided a pharmaceutical composition comprising:
50 to 200 mg RAD001;
100 to 300 mg BEZ235 or CCG168; and
a pharmaceutically acceptable carrier or diluent;
for use in the treatment or prevention of a neurodegenerative disease.

In one embodiment, there is provided a pharmaceutical composition comprising:
25 to 175 mg RAD001;
100 to 250 mg BEZ235 or CCG168; and
a pharmaceutically acceptable carrier or diluent;
for use in the treatment or prevention of a neurodegenerative disease.

In one embodiment, there is provided a pharmaceutical composition comprising:
1 to 200 mg RAD001;
50 to 300 mg BEZ235 or CCG168; and
a pharmaceutically acceptable carrier or diluent;
for use in the treatment or prevention of a neurodegenerative disease.

In one embodiment, there is provided a pharmaceutical composition comprising:
1 to 300 mg RAD001;
1 to 500 mg BEZ235 or CCG168; and
a pharmaceutically acceptable carrier or diluent;
for use in the treatment or prevention of a neurodegenerative disease.

In one embodiment, there is provided a pharmaceutical composition comprising:
1 to 500 mg RAD001;
1 to 800 mg BEZ235 or CCG168; and
a pharmaceutically acceptable carrier or diluent;
for use in the treatment or prevention of a neurodegenerative disease.

In one preferred embodiment of the present invention, the allosteric mTOR inhibitor and the catalytic mTOR inhibitor are administered orally.

In another preferred embodiment of the present invention, the neurodegenerative disease is selected from Huntington's Disease, Parkinson's disease, spinocerebellar ataxia type 3, Alzheimer's disease, motor neuron disease and peripheral neuropathy.

In a further preferred embodiment of the present invention, the neurodegenerative disease is Huntington's Disease.

As used herein, the term "a," "an," "the" and similar terms used in the context of the present invention (especially in the context of the claims) are to be construed to cover both the singular and plural unless otherwise indicated herein or clearly contradicted by the context.

As used herein, the term "about" in connection with a particular drug dose shall have the meaning of a drug dose in the range of plus/minus 10%, preferably plus/minus 5%, more preferably plus/minus 2.5%, or more preferably still plus/minus 1%, of the nominal drug dose. By way of example, a nominal drug dose of about 100 mg active ingredient may contain from 90 to 110 mg, preferably from 95 to 105 mg, more preferably 97.5 to 102.5 mg, or more preferably still 99 to 101 mg active ingredient per dose.

As used herein, the term "allosteric mTOR inhibitor" refers to a compound which targets, decreases or inhibits the activity/function of the mTOR kinase through binding to an allosteric binding site, for example the FKBP12-rapamycin binding site (FRB), of the mTORC1 complex.

Examples of allosteric mTOR inhibitors include Sirolimus (rapamycin, AY-22989), RAD001, 40-[3-hydroxy-2-(hydroxymethyl)-2-methylpropanoate]-rapamycin (also called Temsirolimus or CCI-779) and Deferolimus (AP-23573/MK-8669). Reference to any particular allosteric mTOR inhibitor herein also comprises any pharmaceutically acceptable salts, stereoisomers, tautomers, solvates, hydrates and polymorphs thereof. Whether or not a particular substance is an allosteric inhibitor of mTOR can be assessed using standard enzyme kinetics analysis well know to those skilled in art, Childs et al., (1976), Fersth A. (1985) and Dixon M. (2000). Whether or not a particular substance functions as an allosteric inhibitor by binding to the FRB of the mTORC1 complex can be assessed using the Time-Resolved Fluorescence Resonance Energy Transfer (TR-FRET) assay described hereinafter.

As used herein, the term "BEZ235" also comprises any pharmaceutically acceptable salts, stereoisomers, tautomers, solvates, hydrates and polymorphs thereof. For example, in one embodiment of the present invention, the BEZ235 is provided in its monotosylate salt form.

As used herein, the term "catalytic mTOR inhibitor" refers to a compound which targets, decreases or inhibits the catalytic activity/function of mTOR by binding to its ATP binding site. The term "catalytic mTOR inhibitor" as used herein includes both dual catalytic PI3K/mTOR inhibitors and selective catalytic mTOR inhibitors. Examples of catalytic mTOR inhibitors include BEZ235, 8-(6-methoxy-pyridin-3-yl)-3-methyl-1-(4-piperazin-1-yl-3-trifluoromethyl-phenyl)-1,3-dihydro-imidazo[4,5-c]quinolin-2-one (WO2006/122806), AZD-8055, Ku-0063794 (Garcia-Martinez et al., 2009) and WYE-354 (Yu et al., 2009). Reference to any particular catalytic mTOR inhibitor herein also comprises any pharmaceutically acceptable salts, stereoisomers, tautomers, solvates, hydrates and polymorphs thereof. Whether or not a particular substance is a catalytic inhibitor of mTOR can be assessed using standard enzyme kinetics analysis well know to those skilled in art, Childs et al., (1976), Fersth A. (1985) and Dixon M. (2000).

As used herein, the term "CCG168" also comprises any pharmaceutically acceptable salts, stereoisomers, tautomers, solvates, hydrates and polymorphs thereof.

As used herein, the term "combination" refers to any combination of an allosteric mTOR inhibitor and a catalytic mTOR inhibitor useful in the treatment or prevention of a neurodegenerative disease, for example Huntington's Disease. Any such combination may be administered simultaneously or sequentially. The term "combination" also includes "combination product".

As used herein, the term "combination product" refers to any product which comprises both an allosteric mTOR inhibitor and a catalytic mTOR inhibitor, for example a combined fixed dose pharmaceutical composition which comprises an allosteric mTOR inhibitor and a catalytic mTOR inhibitor as active ingredients, or a kit of parts which comprises individual or combined preparations of an allosteric mTOR inhibitor and a catalytic mTOR inhibitor in forms suitable for simultaneous, separate or sequential administration. A combined fixed dose pharmaceutical composition comprises both an allosteric mTOR inhibitor and a catalytic mTOR inhibitor in a single pharmaceutical composition, for example a single pill or tablet comprising RAD001 and BEZ235 or CCG168.

As used herein, a subject is "in need of" a treatment if such subject would benefit biologically, medically or in quality of life from such treatment.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "mg/kg/day" refers to mg of compound per kg bodyweight of subject per day.

As used herein, the term "preparations of an allosteric mTOR inhibitor and a catalytic mTOR inhibitor" includes pharmaceutical compositions of an allosteric mTOR inhibitor and a catalytic mTOR inhibitor. The term "individual preparations of an allosteric mTOR inhibitor and a catalytic mTOR inhibitor" refers to separate preparations of an allosteric mTOR inhibitor and a catalytic mTOR inhibitor, whereas "a combined preparation of an allosteric mTOR inhibitor and a catalytic mTOR inhibitor" refers to a single preparation comprising both an allosteric mTOR inhibitor and a catalytic mTOR inhibitor, for example a combined fixed dose pharmaceutical composition which comprises both an allosteric mTOR inhibitor and a catalytic mTOR inhibitor, for example RAD001 and BEZ235 or CCG168 in a single pill or tablet.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

As used herein, the term "prevention" of any particular disease or disorder refers to the administration of a compound of the invention to a subject before any symptoms of that disease or disorder are apparent.

As used herein, the term "RAD001" also comprises any pharmaceutically acceptable salts, stereoisomers, tautomers, solvates, hydrates and polymorphs thereof.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof) in a subject by administration of a combination according to the present invention. In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The compounds of the combinations of the present invention may be administered either simultaneously or sequentially. The compounds of the combinations of the present invention may also be administered separately, by the same or different route of administration, or together in the same pharmaceutical composition.

A kit of parts of the present invention comprises means for separately retaining individual or combined preparations of an allosteric mTOR inhibitor and a catalytic mTOR inhibitor, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

The allosteric mTOR inhibitor and catalytic mTOR inhibitor of the combinations of the invention may be brought together into a combination therapy: (i) prior to release of the combination product to physicians (e.g. in the case of a kit); (ii) by the physician themselves (or under the guidance of the physician) shortly before administration; or (iii) in the patient themselves, e.g. during sequential administration of an allosteric mTOR inhibitor and a catalytic mTOR inhibitor.

The pharmaceutical composition of the present invention can be formulated for particular routes of administration such as oral administration, parenteral administration, and rectal administration, etc. In one preferred embodiment of the present invention, the allosteric mTOR inhibitor and the catalytic mTOR inhibitor are administered orally. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredients together with
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and/or
  e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient(s) in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

An individual pharmaceutical composition comprising BEZ235 may be provided as a hard gelatin capsule for oral administration comprising 5, 25 or 100 mg of BEZ235. The excipients may be: lactose, crospovidone, Polyvinyl pyrrolidone K30, starch, Aerosil and magnesium stearate. The 5 and 25 mg capsules may use a Size 4 size capsule shell; the 100 mg capsule may use a size 1 capsule shell.

RAD001 is an FDA approved drug and therefore suitable individual pharmaceutical compositions comprising of RAD001 are commercially available. For example, RAD001 can be administered in tablet form for oral administration in a tablet comprising a suitable amount of RAD001 and butylated hydroxytoluene (BHT), magnesium stearate, hydroxypropyl methylcellulose, crospovidone and lactose as excipients. RAD001 can also be administered as a dispersable tablet comprising a suitable amount of RAD001 and BHT, magnesium stearate, hydroxypropyl methylcellulose, crospovidone, colloidal anhydrous silica and lactose as excipients.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising an allosteric mTOR inhibitor and a catalytic mTOR inhibitor as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers,"

The dosages of an allosteric mTOR inhibitor and a catalytic mTOR inhibitor of the pharmaceutical compositions and combinations of the present invention are dependent on the species of the subject, the body weight, age and individual condition, or the severity of disease being treated. A physician, clinician or veterinarian of ordinary skill can readily determine the effective amount of each of the active ingredients necessary to prevent, treat or inhibit the progress of disease.

The above-cited dosage properties may be demonstrated in in vitro and in vivo tests using advantageously mammals, e.g., mice, rats, dogs, monkeys or isolated organs, tissues and preparations thereof. The compounds of the combinations of the present invention may be applied in vitro in the form of solutions, e.g., aqueous solutions, and in vivo either enterally, parenterally, advantageously intravenously, e.g., as a suspension or in aqueous solution. The dosage concentrations in vitro for RAD001 may range between 1 to 500 nM, 100 to 350 nM, 200 to 200 nM, or about 250 nM, whereas the dosage concentrations in vitro for BEZ235 or CCG168 may range between 1 to 200 nM, 1 to 100 nM, 25 to 75 nM, or about 50 nM. Dosage concentrations in vivo are provided hereinbefore.

EXAMPLES

Example 1

Low-Dose Combination of RAD001 and BEZ235 or CCG168 Induces Autophagy in R6/2 Brain Slices Recent studies have shown that autophagy is a key clearance pathway for mHtt accumulation and that the inhibition of the mTOR pathway is sufficient to induce autophagy. In particular, inhibitors of the mTOR pathway were shown to induce autophagy, decrease mHtt accumulation and protect from neurodegeneration in different cellular, fly and animal models of Huntington disease (Ravikumar et al., 2004; Ravikumar et al., 2006; Levine et al., 2008; Sakar et al., 2009). To evaluate whether allosteric and catalytic mTOR inhibitors could induce autophagy and preserve striatal degeneration, R6/2 slices were treated using RAD001, BEZ235 and CCG168 ({5-[2,4-bis-((S)-3-methyl-morpholin-4-yl)-pyrido[2,3-d]pyrimidin-7-yl]-2-methoxy-phenyl}-methanol) from DIV14 to DIV21 and the mTOR activity and LC3-II/I conversion at DIV21 analysed (FIG. 1). 300 nM BEZ235 and 300 nM CCG168 induced autophagy, whereas 250 nM RAD001 and 50 nM BEZ235 had no effect. Interestingly, 50 nM BEZ235 did not reduce the level of p-S6 S240/244 in contrast to 250 nM RAD001 and 250 nM RAD001/50 nM BEZ235. Surprisingly, the combinations of 250 nM RAD001/50 nM BEZ235 and 250 nM RAD001/50 nM CCG168 were sufficient to induce autophagy compared to 250 nM RAD001 and 50 nM BEZ235 single concentrations, indicating that BEZ235 and CCG168 work synergistically with RAD001 in increasing LC3-II levels (FIG. 1).

Example 2

Low-Dose Combination of RAD001 and BEZ235 or CCG168 Reduces polyQ Inclusions in R6/2 Brain Slices In order to investigate whether the combination of RAD001/BEZ235 could work synergistically in reducing polyQ inclusions, the polyQ density of treated R6/2 slices at DIV21 was measured by comparing the immunohistochemical detection of PolyQ inclusions and nuclei in R6/2 slices. Slices treated with 250 nM RAD001 or 50 nM BEZ235 exhibited a similar polyQ distribution compared to control R6/2, whereas the combination of RAD001/BEZ235 and RAD001/CCG168 reduced the polyQ density. It was observed that single low-concentrations of RAD001 and BEZ235 did not reduce polyQ inclusions, whereas the combination had a significant effect and reduced 40%±11 of the polyQ density compared to R6/2 slices. In addition, the effective single concentration of 300 nM BEZ235 lead to a similar decrease, suggesting that BEZ235 together with RAD001 worked synergistically in reducing polyQ density (FIG. 2).

Example 3

Low-Dose Combination of RAD001 and BEZ235 or CCG168 Prevents Striatal Degeneration in R6/2 Brain Slices HD progression is characterized by the gradual loss of striatal DARPP-32 and axonal degeneration (The Huntington's Disease Collaborative Research Group. 1993; Davies et al., 1997; Bibb et al., 2000; Luthi-Carter et al., 2000). In R6/2 slices, a gradual loss of striatal DARPP-32 and neurofilament starting at DIV21 was monitored. Therefore, to assess whether the combination of RAD001/BEZ235 could preserve synergistically the on going striatal degeneration, DARPP-32 and neurofilament stainings at DIV21 were analysed by immunohistochemical detection of DARPP-32 and neurofilament in WT and R6/2 slices. Single low-concentrations of RAD001 and BEZ235 were ineffective in preserving DARPP-32 and neurofilament levels. However, the combination preserved 95%±12 of the neurofilament level and 80%±5 of the DARPP-32 level. 250 nM RAD001/30 nM BEZ235 was the lowest effective combinatorial concentration (FIGS. 3 and 4). A combination of 250 nM RAD001 and 50 nM CCG168 was also effective in preserving DARPP-32 and neurofilament levels.

Conclusion

Taken together these results indicate that the combination of an allosteric mTOR inhibitor and a catalytic mTOR inhibitor, for example RAD001/BEZ235 or CCG168, works synergistically to induce autophagy, reduce polyQ inclusions and preserve striatal degeneration and surprisingly allows efficacy at a lower concentration compared to a catalytic mTOR inhibitor alone, for example a 10 fold lower concentration compared to 300 nM BEZ235. Thus, low-dose combinations of an allosteric mTOR inhibitor and a catalytic mTOR inhibitor represent an opportunity to cure HD and other neurodegenerative diseases caused by aggregate-prone proteins with a reduced drug exposure.

Experimental Procedures

Examples 1 to 3 above were carried out using the following experimental procedures Mice and Slice Cultures Transgenic mice expressing human Huntingtin Exon-1Q200 (R6/2 mouse model described in Davies et al., 1997) were housed in a temperature-controlled room and maintained on a 12 hr light/dark cycle. Food and water were available ad libitum and experiments were carried out in accordance with the local authorization guidelines for the care and use of laboratory animals. Slice cultures were established according to the procedure described by Stoppini and colleagues (Stoppini et al., 1991 and Gogolla et al., 2006) and a particular cutting angle was utilized to produce brain slices with a preserved cortico-striatal pathway. Finally, slices were selected, placed on Millicel (Millipore, PICM03050) and cultured in 6-well dishes at 35° C. and 5% $CO_2$ in the presence of 1 ml of culture medium.

Treatment with mTOR Inhibitors

Slices were treated with different mTOR inhibitors from DIV14 to DIV21. The culture medium was exchanged every second day, and drugs were added in the fresh culture medium. We used this protocol to evaluate the action of the following mTOR inhibitors: BEZ235 (50 and 300 nM in DMSO), RAD001 (250 nM in DMSO), CCG168 (300 nM in DMSO), RAD001+BEZ235 (250 10, 250 30 and 250 50 nM in DMSO) and RAD001'CCG168 (250 and 50 nM in DMSO).

Biochemistry

Slices were washed in PBS and lysed in 1% Triton X-100/PBS containing Complete Mini (Roche, #04693124001) and PhosSTOP (Roche, #04906837001). Lysates were ultrasonicated and analysed by Western blotting for B-actin (Sigma, #A5441), pS6 Ser 240/244 (Cell Signalling, #2215), and LC3B (Cell Signalling, #2775). Immunoblots were developed with ECL detection reagent (Amersham Biosciences).

Immunohistochemistry

Slices were fixed for 10 minutes in 4% PFA, washed in PBS and blocked for 4 hr at room temperature in 0.3% Triton X-100 20% Horse Serum/PBS (blocking solution). Antibodies for DARPP-32 (Cell Signaling, #2306S, 1:200), neurofilament (NeuF, Developmental Studies Hybridoma Bank, University of Iowa; #2H3, 1:200) and EM48 (Millipore, #MAB5374, 1:200) were incubated for 48 hr at 4° C. in the blocking solution. Afterwards, slices were washed in PBS, incubated for 2 hrs in 0.3% Triton X-100/PBS with Alexa 488 (Invitrogen, 1:500) and Alexa 555 (Invitrogen, 1:500) conjugated secondary antibodies. Finally, slices were washed in PBS, incubated 10 minutes with DAPI (Invitrogen, #D1306 1:10000) and embedded on glass dishes using ProLong (Invitrogen, #P36934).

Microscopy and Quantification

High resolution images were acquired on an upright Zeiss LSM700 confocal microscope, using a Plan-Neofluar 40×/1.3 oil immersion objective. For the quantification of the PolyQ density and DARPP-32/NeuF signal intensity, at least three confocal 3D stacks/slice were acquired in striatum for each experiment (five slices per condition), and analyzed using Imaris 4.2 (Bitplane AG) and Image J softwares.

Statistical Analysis

All data are expressed as mean±SEM. Statistical analysis was performed by analysis of variance (ANOVA) followed by a Student's t Test (Excel, Microsoft, USA). The significance level was set at $p<0.05$.

mTOR Assay by TR-FRET

Reagents and Instrumentation: The TR-FRET mTOR binding assay components may be purchased from Invitrogen Corporation (Carlsbad/Calif., USA): GFP-FKBP12 (sample 691-145-3B, 47 µM, MW=38 KDa), $Tb^{3+-}\alpha$-GST Antibody (Cat. No. PV4216), proprietary TR-FRET dilution buffer (Cat. No. PV3574), GFP-4EBP1 (Cat. No. PV4759). DMSO (Fluka, Cat. No. 41644). A Synergy 2 microplate reader from Biotek Instruments, Winooski, Vt. (obtained through Witec, Switzerland) with the following settings may be used: detection method Fluorescence Time resolved, light source Xenon flash, read type End point, read speed Normal, delay after plate movement 100 msec, delay before collecting data 100 µs, measurements per data point 10, data collection time 200 µs, sensitivity auto, excitation filter 340/30, emission filters 520/25 and 495/10.

Black non-binding polystyrene plates in 384-well format for the TR-FRET mTOR binding assay are available from Corning (low volume, round bottom, Cat. No. NBS#3676).

Sample inhibitor compounds are prepared freshly as 10 mM solutions in DMSO.

Compounds from 10 mM stock are diluted in DMSO first, then in TR-FRET buffer.

Assay Plates:

Compounds are directly diluted in the 384-well assay plate and final concentration of DMSO is kept constant at 1%. The compounds in dilution are mixed with 10 µL of GFP-FKBP-12, $Tb^{3+-}\alpha$-GST antibody and GST-mTOR. The final volume in the assay plate is 20 µl.

Principle:

Time-Resolved Fluorescence Resonance Energy Transfer (TR-FRET) is a technology based on energy transfer between two adjacent dyes, from an excited electron in one dye (the donor) to an electron of an adjacent dye (the acceptor) through resonance, then released as a photon. This energy transfer is detected by an increase in the fluorescence emission of the acceptor, and a decrease in the fluorescence emission of the donor.

TR-FRET assays use a long-lifetime lanthanide chelates or cryptates as the donor species which overcome interference from compound autofluorescence or light scatter from precipitated compounds, by introducing a delay after excitation by a flashlamp excitation source. Results are often expressed as a ratio of the intensities of the acceptor and donor fluorophores (520 nm/495 nm). The ratiometric nature of such a value corrects for differences in assay volumes between wells, as well as corrects for quenching effects due to colored compounds.

mTOR Binding Assay by TR-FRET:

10 µL of inhibitor compound dilutions are mixed with 10 µL of GFP-FKBP12, $Tb^{3+-}\alpha$-GST antibody and GST-mTOR in TR-FRET buffer and incubated for 60 mins at room temperature protected from light before reading. Plates are read in a Synergy2 reader using an integration time of 200 µs and a delay of 100 µs. The following controls are performed to give the basis signal including assay with 2% DMSO (without compound), assay without GST-mTOR, assay with GFP-4EBP1 (without GFP-FKBP12).

GFP-FKBP12 binds to mTOR when complexed with an allosteric mTOR inhibitor that binds to the FRB of the mTORC1 complex, for example rapamycin. The mTOR binding assay uses a specific anti-GST-Ab labeled with $Tb^{3+}$ that recognizes the GST tagged mTOR. The TR-FRET assays use this long-lifetime $Tb^{3+}$ chelate as the donor species to transfer the energy to the GFP-FKBP12 resulting in an acceptor and donor emission of 520 nm and 495 nm, respectively. Results are expressed as a ratio of the intensities of the acceptor and donor fluorophores.

Determination of $EC_{50}$:

$EC_{50}$ values of the percentage inhibition of each potential allosteric mTOR inhibitor compound may be derived by fitting a sigmoidal dose-response curve (variable slope) to a plot of assay readout over inhibitor concentration.

Expression and Purification of Human GST-mTOR and GFP-FKBP12

| Human TOR | UniProtKB/Swiss-Prot: P42345; NCBI/Protein Database: NP002638 |
| --- | --- |
| FKBP12 | UniProtKB/Swiss-Prot: P62942 |
| 4-EBP1 | UniProtKB/Swiss-Prot: Q13541 |

GST-mTOR (1360-2549):

N terminally tagged GST-mTOR and GFP-FKBP12 were purchased from Invitrogen Recombinant human N-terminally truncated (amino acids 1360-2549) GST-tagged mTOR was expressed in insect cells and obtained from Invitrogen (PV4753, MW=163.9 kDa).

His-GFP-FKBP12:

The GFP-FKBP12 was also obtained from Invitrogen (sample 691-145-3B, 47 µM, MW=43 KDa).

His-GFP-4-EBP1:

The GFP-4-EBP1 was also obtained from Invitrogen (Cat. No. PV4759, MW=45 KDa).

REFERENCES

Bibb J A, Yan Z, Svenningsson P, Snyder G L, Pieribone V A, Horiuchi A, Nairin A C, Messers A, and Greengard P. (2000). Severe deficiencies in dopamine signaling in presymptomatic Huntington's disease mice. PNAS 97: (12) 6809-6814.

Chresta C M, Davies B R, Hickson I, Harding T, Cosulich S, Critchlow S E, Vincent J P, Ellston R, Jones D, Sini P, James D, Howard Z, Dudley P, Hughes G, Smith L, Maguire S, Hummersone M, Malagu K, Menear K, Jenkins R, Jacobsen M, Smith G C M, Guichard S and Pass M. (2010). AZD8055 Is a Potent, Selective, and Orally Bioavailable ATP-Competitive Mammalian Target of Rapamycin Kinase Inhibitor with In vitro and In vivo Antitumor Activity. Cancer Research 70(1), 288-298.

Davies S W, Turmaine M, Cozens B A, DiFiglia M, Sharp A H, Ross C A, Scherzinger E, Wanker E E, Mangiarini L and Bates G P. (1997). Formation of neuronal intranuclear inclusions underlies the neurological dysfunction in mice transgenic for the HD mutation. Cell 90: 537-48.

Galimberti I, Bednarek E, Donato F, and Caroni P (2010). EPHA4 signaling in juveniles establishes topographic specificity of structural plasticity in the Hippocampus. Neuron. 65, 627-642.

Galimberti I, Gogolla N, Alberi S, Santos A F, Muller D, and Caroni P (2006). Long-term rearrangements of hippocampal mossy fiber terminal connectivity in the adult regulated by experience. Neuron. 50, 749-763.

Garcia-Martinez J M, Moran J, Clarke R G, Gray A, Cosulich S C, Chresta C M and Alessi D R (2009). Ku-0063794 is a specific inhibitor of the mammalian target of rapamycin (mTOR). Biochem J. 421(1), 29-42.

Gogolla N, Galimberti I, DePaola V, and Caroni P (2006a). Preparation of organotypic hippocampal slice cultures for long-term live imaging. Nat. Protoc. 1, 1165-1171.

Hara T, Nakamura K, Matsui M, Yamamoto A, Nakahara Y, Suzuki-Migishima R, Yokoyama M, Mishima K, Saito I, Okano H, Mizushima N (2006). Suppression of basal autophagy in neural cells causes nerodegenerative disease in mice. Nature. 441, 885-9.

Levine B, and Kroemer G (2008). Autophagy in the pathogenesis of disease. Cell 132, 27-42.

Luthi-Carter R, A Strand, N L Peters, S M Solano, Z R Hollingsworth, A S Menon, A S Frey, B S Spektor, E B Penney, G S chilling, C A Ross, D R Borchelt, S J Tapscott, A B Young, J H Cha, and J M Olson (2000). Decreased expression of striatal signaling genes in a mouse model of Huntington's disease. Hum. Mol. Genet. 9, 1259-1271.

Ravikumar B, Vacher C, Berger Z, Davies J. E, Luo S, Oroz, L. G, Scaravilli F, Easton D. F, Duden R, O'Kane C. J, and Rubinsztein D. C (2004). Inhibition of mTOR induces autophagy and reduces toxicity of polyglutamine expansions in fly and mouse models of Huntington disease. Nat. Genet. 36, 585-595.

Ravikumar B, and D. C. Rubinsztein (2006). Role of autophagy in the clearance of mutant huntingtin: a step towards therapy? Mol. Aspects Med. 27, 520-527.

Rubinsztein D C, Gestwicki J E, Murphy L O, Klionsky D J (2007). Potential therapeutic applications of autophagy. Nat Rev Drug Discov. 6, 304-12.

Sarkar S, Ravikumar B, Rubinsztein D C (2009). Authophagic clearance of aggregate-prone proteins associated with nerodegeneration. Methods Enzymol. 453, 83-110.

Sarkar S, Rubinsztein D C (2008). Huntington's disease: degradation of mutant huntingtin by autophagy. FEBS J. 275, 4263-70.

Serra V, Markman B, Scaltriti M, Eichhorn P, Valero V, Guzman M, Botero M L, Llonch E, Atzori F, Di Cosimo S, Maira M, Garcia-Echeverria C, Parra J L, Arribas J, Baselga J (2008). NVP-BEZ235, a dual PI3K/mTOR inhibitor, prevents PI3K signaling and inhibits the growth of cancer cells with activating PI3K mutations. Cancer Res. 68(19), 8022-8030.

Stoppini L, Buchs P A and Muller D (1991). A simple method for organotypic cultures of nervous tissue. J. Neurosci. Methods. 37, 173-182.

The Huntington's Disease Collaborative Research Group (1993). A novel gene containing a trinucleotide repeat that is expanded and unstable on Huntington's disease chromosomes. Cell. 72, 971-983.

Tsvetkov A S, Miller J, Arrasate M, Wong J S, Pleiss M A, Finkbeiner S (2010). A small-molecule scaffold induces autophagy in primary neurons and protects against toxicity in a Huntington disease model. Proc Natl Acad Sci USA. 107, 16982-16987.

Yu K, Toral-Barza L, Shi C, Zhang W G, Lucas J, Shor B, Kim J, Veheijen J, Curran K, Malwitz D J, Cole D C, Ellingboe J. Ayral-Kaloustian S, Mansour T S, Gibbons J J, Abraham R T, Nowak P and Zask A (2009). Biochemical, Cellular, and In vivo Activity of Novel ATP-Competitive and Selective Inhibitors of the Mammalian Target of Rapamycin Cancer Res. 69(15): 6232-6240.

Yu L. McPhee C K, Zheng L. Mardones G A, Rong Y, Peng J. Mi N. Zhao Y, Liu Z. Wan F. Hailey D W, Oorschot V, Klumperman J, Baehrecke E H, Lenardo M J. (2010). Termination of autophagy and reformation of lysosomes regulated by mTOR. Nature. 465, 942-6.

The invention claimed is:

1. A method for the treatment of Huntington's disease in a subject in need of such treatment, which method comprises administering to such subject a synergistically effective amount of a combination of an allosteric mTOR inhibitor and a catalytic mTOR inhibitor, wherein the allosteric mTOR inhibitor is RAD001 and the catalytic mTOR inhibitor is BEZ235.

2. The method according to claim 1 wherein:

the RAD001 is administered at a dose of between 1.4 and 1.6 mg/kg/day and the BEZ235 is administered at a dose of between 2.4 and 2.6 mg/kg/day;

the RAD001 is administered at a dose of between 1.3 and 1.7 mg/kg/day and the BEZ235 is administered at a dose of between 2.3 and 2.7 mg/kg/day;

the RAD001 is administered at a dose of between 1.2 and 1.8 mg/kg/day and the BEZ235 is administered at a dose of between 2.2 and 2.8 mg/kg/day;

the RAD001 is administered at a dose of between 1.1 and 1.9 mg/kg/day and the BEZ235 is administered at a dose of between 2.1 and 2.9 mg/kg/day;

the RAD001 is administered at a dose of between 1.0 and 2.0 mg/kg/day and the BEZ235 is administered at a dose of between 2.0 and 3.0 mg/kg/day;

the RAD001 is administered at a dose of between 0.8 and 2.2 mg/kg/day and the BEZ235 is administered at a dose of between 1.8 and 2.6 mg/kg/day;

the RAD001 is administered at a dose of between 0.6 and 2.4 mg/kg/day and the BEZ235 is administered at a dose of between 1.6 and 2.8 mg/kg/day;

the RAD001 is administered at a dose of between 0.4 and 2.6 mg/kg/day and the BEZ235 is administered at a dose of between 1.4 and 3.0 mg/kg/day;

the RAD001 is administered at a dose of between 0.2 and 2.8 mg/kg/day and the BEZ235 is administered at a dose of between 1.0 and 3.5 mg/kg/day;

the RAD001 is administered at a dose of between 0.01 and 3.0 mg/kg/day and the BEZ235 is administered at a dose of between 0.5 and 4.0 mg/kg/day;

the RAD001 is administered at a dose of between 0.01 and 5.0 mg/kg/day and the BEZ235 is administered at a dose of between 0.01 and 5.0 mg/kg/day; or the RAD001 is administered at a dose of between 0.01 and 10.0 mg/kg/day and the BEZ235 is administered at a dose of between 0.01 and 10.0 mg/kg/day.

3. The method according to claim 1 wherein the RAD001 is administered at a dose of between 0.01 and 3.0 mg/kg/day and the BEZ235 is administered at a dose of about 2.5 between 0.01 and 10.0 mg/kg/day.

4. The method according to claim 3 wherein the RAD001 and the BEZ235 are administered orally.

* * * * *